US007270825B2

(12) United States Patent
Pogue et al.

(10) Patent No.: US 7,270,825 B2
(45) Date of Patent: *Sep. 18, 2007

(54) PRODUCTION OF A PARVOVIRUS VACCINE IN PLANTS AS VIRAL COAT PROTEIN FUSIONS

(75) Inventors: Gregory P. Pogue, Vacaville, CA (US); John A. Lindbo, Vacaville, CA (US); Michael J. McCulloch, Vacaville, CA (US); Jonathan E. Lawrence, Vacaville, CA (US); Cynthia S. Gross, Vacaville, CA (US); Stephen J. Garger, Vacaville, CA (US)

(73) Assignee: Large Scale Biology Corporation, Vacaville, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/193,142

(22) Filed: Jul. 12, 2002

(65) Prior Publication Data

US 2002/0192226 A1 Dec. 19, 2002

Related U.S. Application Data

(63) Continuation of application No. 09/520,967, filed on Mar. 8, 2000.

(51) Int. Cl.
*A61K 39/23* (2006.01)
*A61K 39/12* (2006.01)
*A61K 38/00* (2006.01)

(52) U.S. Cl. .................... 424/233.1; 424/186.1; 530/300; 530/350

(58) Field of Classification Search ............ 424/233.1, 424/186.1, 192.1, 278.1; 530/300, 350; 536/23.4, 536/23.6, 23.72

See application file for complete search history.

(56) References Cited

U.S. PATENT DOCUMENTS

| 4,921,802 A | 5/1990 | Hall et al. ............... 435/252.3 |
| 5,785,974 A * | 7/1998 | Casal Alvarez et al. . 424/233.1 |
| 5,977,438 A * | 11/1999 | Turpen et al. ............. 800/288 |

FOREIGN PATENT DOCUMENTS

| EP | 0726312 | 8/1996 |
| WO | WO96/12028 | 4/1996 |
| WO | WO97/39134 | 10/1997 |
| WO | WO97/49425 | 12/1997 |
| WO | WO99/46288 | 9/1999 |

OTHER PUBLICATIONS

Casal Alvarez et al. (sequence alignment of SEQ ID No. 1 with Geneseq accession No. AAR63025, submitted Mar. 17, 1995 in WO 94/17098).*
Casal Alvarez et al. (sequence alignment of SEQ ID No. 2 with Geneseq accession No. AAR63031, submitted Mar. 17, 1995 in WO 94/17098).*
Koo et al. PNAS. 1999; 96: 7774-7779.*
Turpen et al. Bio/Technology. 1995; 13: 53-57.*
Dalsgaard et al. Nature Biotechnology. Mar. 1997; 15: 246-252.*
Sequence alignment of a peptide comprising at least amino acids 3-16 of SEQ ID No. 1 with Geneseq database accession No. AAR63026 of Casal Alvarez et al. submitted Mar. 17, 1995 in WO 94/17098-A1.*
Sequence alignment of a peptide comprising at least amino acids 3-17 of SEQ ID No. 2 with Geneseq database accession No. AAR63031 of Casal Alvarez et al. submitted Mar. 17, 1995 in WO 94/17098-A1.*
Baker, et al., "Polyethylenimine (PEI) is a simple, inexpensive and effective reagent for condensing and linking plasmid DNA to adenovirus for gene delivery", *Gene Therapy* (1997) 4(8):773-82.
Fitchen, et al., "Plant virus expressing hybrid coat protein with added murine epitope elicits autoantibody response", *Vaccine* (1995) 13(12):1051-57.
Girard and Hirth, "Methodes d'etudes des virus", *Virologie Moleculaire* (1989) pp. 61-65.
Hansen, "Production of recombinant antigens in plants for animal and human immunication—a review", *Brazilian J. of Gen.* (1997) 20(4):703-711.
Jerala, et al., "Improved expression and evaluation of polyethyleneimine precipitation in isolation of recombinant cysteine proteinase inhibitor stefin B", *Protein Exp. and Purif.* (1994) 5:65-69.
Langeveld, et al., "Effective induction of neutralizing antibodies with the amino terminus of VP2 of canine parvovirus as a synthetic peptide", *Vaccine* (1994) 12(15):1473-08.

* cited by examiner

*Primary Examiner*—Shanon Foley
(74) *Attorney, Agent, or Firm*—John E. Tarcza; Wayne P. Fitzmaurice

(57) ABSTRACT

The present invention relates to foreign peptide sequences fused to recombinant plant viral structural proteins and a method of their production. Fusion proteins are economically synthesized in plants at high levels by biologically contained tobamoviruses. The fusion proteins of the invention have are useful as antigens for inducing the production of antibodies having desired binding properties, e.g., protective antibodies, or for use as vaccine antigens for the induction of protective immunity against the parvovirus. Feline parvovirus epitopes were fused to the N-terminus of the TMV coat protein, expressed in *Nicotiana* plants, extracted, purified, characterized and administered to animals, resulting in protective immunity.

15 Claims, 6 Drawing Sheets

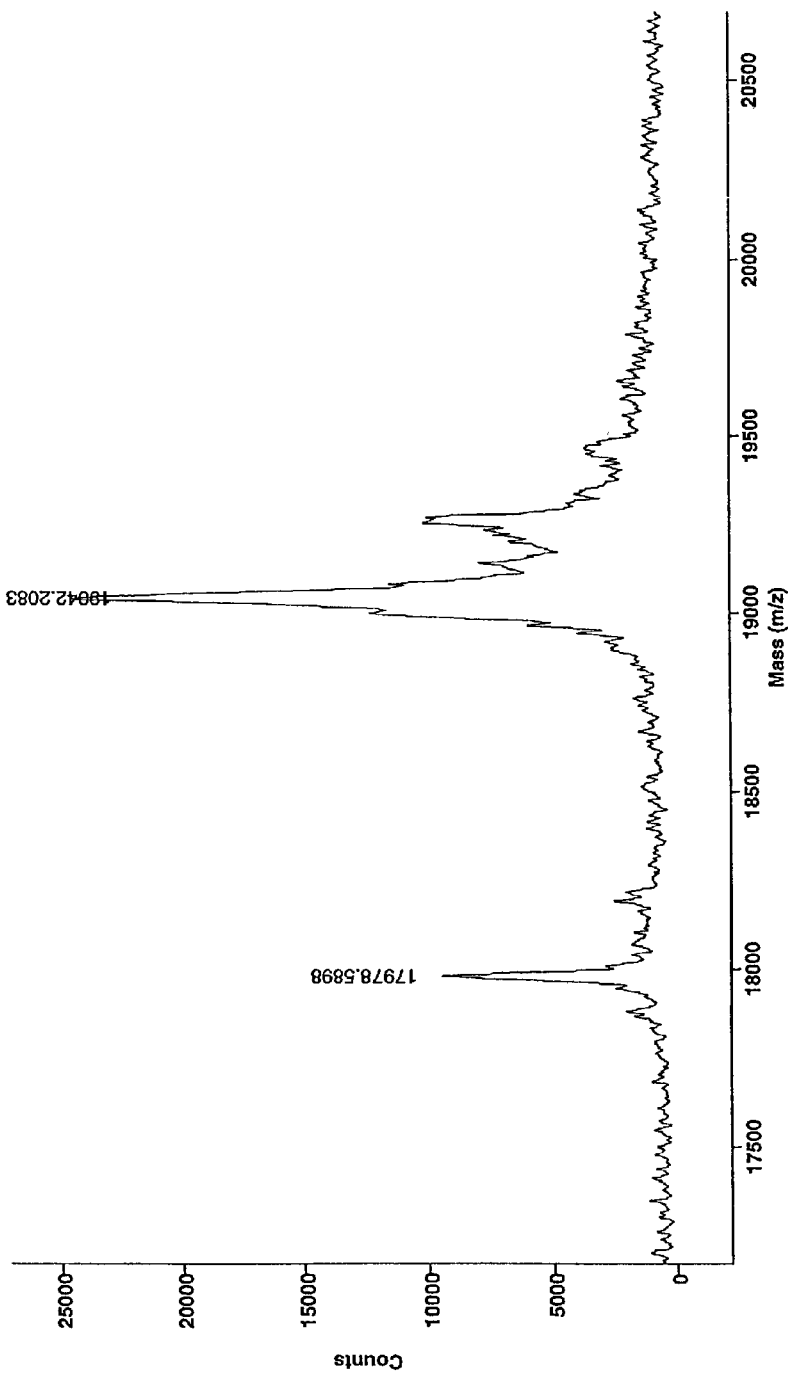

SEQUENCE LISTING

<160> NUMBER OF SEQ ID NOS: 23

<210> SEQ ID NO 1
<211> LENGTH: 16
<212> TYPE: PRT
<213> ORGANISM: Artificial Sequence
<220> FEATURE:
<221> NAME/KEY: misc_feature
<222> LOCATION: ()..()
<223> OTHER INFORMATION: fusion protein -continued

```
<400> SEQUENCE: 1

Met Gly Ser Asp Gly Ala Val Gln Pro Asp Gly Gly Gln Pro Ala Val
1               5                   10                  15

<210> SEQ ID NO 2
<211> LENGTH: 17
<212> TYPE: PRT
<213> ORGANISM: Artificial Sequence
<220> FEATURE:
<221> NAME/KEY: misc_feature
<222> LOCATION: ()..()
<223> OTHER INFORMATION: fusion protein

<400> SEQUENCE: 2

Met Gly Gln Pro Asp Gly Gly Gln Pro Ala Val Arg Asn Glu Arg Ala
1               5                   10                  15

Thr

<210> SEQ ID NO 3
<211> LENGTH: 49
<212> TYPE: DNA
<213> ORGANISM: Artificial Sequence
<220> FEATURE:
<221> NAME/KEY: misc_feature
<222> LOCATION: ()..()
<223> OTHER INFORMATION: primer

<400> SEQUENCE: 3
ggaattcaag cttaatacga ctcactatag tattttttaca acaattacc            49

<210> SEQ ID NO 4
<211> LENGTH: 18
<212> TYPE: DNA
<213> ORGANISM: Artificial Sequence
<220> FEATURE:
<221> NAME/KEY: misc_feature
<222> LOCATION: ()..()
<223> OTHER INFORMATION: primer

<400> SEQUENCE: 4
ccttcatgta aacctctc                                               18

<210> SEQ ID NO 5
<211> LENGTH: 57
<212> TYPE: DNA
<213> ORGANISM: Artificial Sequence
<220> FEATURE:
<221> NAME/KEY: misc_feature
<222> LOCATION: ()..()
<223> OTHER INFORMATION: synthetic plasmid

<400> SEQUENCE: 5
taaatattct taagccagta gtatgggata tccagtggta tgggatccta cagtatc     57

<210> SEQ ID NO 6
<211> LENGTH: 12
<212> TYPE: DNA
<213> ORGANISM: Artificial Sequence
<220> FEATURE:
<221> NAME/KEY: misc_feature
<222> LOCATION: ()..()
<223> OTHER INFORMATION: synthetic plasmid

<400> SEQUENCE: 6
ccagtagtat gg                                                     12
```

```
<210> SEQ ID NO 7
<211> LENGTH: 12
<212> TYPE: DNA
<213> ORGANISM: Artificial Sequence
<220> FEATURE:
<221> NAME/KEY: misc_feature
<222> LOCATION: ()..()
<223> OTHER INFORMATION: synthetic plasmid

<400> SEQUENCE: 7
ccagtggtat gg                                                            12

<210> SEQ ID NO 8
<211> LENGTH: 50
<212> TYPE: DNA
<213> ORGANISM: Artificial Sequence
<220> FEATURE:
<221> NAME/KEY: misc_feature
<222> LOCATION: ()..()
<223> OTHER INFORMATION: primer

<400> SEQUENCE: 8
tgggatatcc agtggtatgg gatcctacag tatacactac tccatctcag                   50

<210> SEQ ID NO 9
<211> LENGTH: 30
<212> TYPE: DNA
<213> ORGANISM: Artificial Sequence
<220> FEATURE:
<221> NAME/KEY: misc_feature
<222> LOCATION: ()..()
<223> OTHER INFORMATION: primer

<400> SEQUENCE: 9
cgcgtacctg ggcccctacc gggggtaacg                                         30

<210> SEQ ID NO 10
<211> LENGTH: 27
<212> TYPE: DNA
<213> ORGANISM: Artificial Sequence
<220> FEATURE:
<221> NAME/KEY: misc_feature
<222> LOCATION: ()..()
<223> OTHER INFORMATION: primer

<400> SEQUENCE: 10
ggcccatgga acttacagaa gaagtcg                                            27

<210> SEQ ID NO 11
<211> LENGTH: 57
<212> TYPE: DNA
<213> ORGANISM: Artificial Sequence
<220> FEATURE:
<221> NAME/KEY: misc_feature
<222> LOCATION: ()..()
<223> OTHER INFORMATION: primer

<400> SEQUENCE: 11
ctggatatcc catactactg gcttaagaat atttaaaacg aatccgattc ggcgaca           57

<210> SEQ ID NO 12
<211> LENGTH: 91
<212> TYPE: DNA
<213> ORGANISM: Artificial Sequence
<220> FEATURE:
<221> NAME/KEY: misc_feature
<222> LOCATION: ()..()
<223> OTHER INFORMATION: primer
```

```
<400> SEQUENCE: 12
cctgggccag tagtatgggt tcagatggtg ctgtacaacc agatggaggt caaccagctg      60
tatcttacag tatcactact ccatctcagt t                                    91

<210> SEQ ID NO 13
<211> LENGTH: 91
<212> TYPE: DNA
<213> ORGANISM: Artificial Sequence
<220> FEATURE:
<221> NAME/KEY: misc_feature
<222> LOCATION: ()..()
<223> OTHER INFORMATION: primer

<400> SEQUENCE: 13
cctgggccag tagtatgggt tcagatggtg ctgtacaacc agatggaggt caaccagctg      60
tatcttacag tatcactact ccatctcagt t                                    91

<210> SEQ ID NO 14
<211> LENGTH: 24
<212> TYPE: PRT
<213> ORGANISM: Artificial Sequence
<220> FEATURE:
<221> NAME/KEY: misc_feature
<222> LOCATION: ()..()
<223> OTHER INFORMATION: fusion protein

<400> SEQUENCE: 14

Gly Ser Asp Gly Ala Val Gln Pro Asp Gly Gly Gln Pro Ala Val Ser
1               5                   10                  15

Tyr Ser Ile Thr Thr Pro Ser Gln
            20

<210> SEQ ID NO 15
<211> LENGTH: 23
<212> TYPE: PRT
<213> ORGANISM: Artificial Sequence
<220> FEATURE:
<221> NAME/KEY: misc_feature
<222> LOCATION: ()..()
<223> OTHER INFORMATION: fusion protein

<400> SEQUENCE: 15

Ser Asp Gly Ala Val Gln Pro Asp Gly Gly Gln Pro Ala Val Ser Tyr
1               5                   10                  15

Ser Ile Thr Thr Pro Ser Gln
            20

<210> SEQ ID NO 16
<211> LENGTH: 21
<212> TYPE: PRT
<213> ORGANISM: Artificial Sequence
<220> FEATURE:
<221> NAME/KEY: misc_feature
<222> LOCATION: ()..()
<223> OTHER INFORMATION: fusion protein

<400> SEQUENCE: 16

Gly Ala Val Gln Pro Asp Gly Gly Gln Pro Ala Val Ser Tyr Ser Ile
1               5                   10                  15

Thr Thr Pro Ser Gln
            20

<210> SEQ ID NO 17
```

-continued

```
<211> LENGTH: 20
<212> TYPE: PRT
<213> ORGANISM: Artificial Sequence
<220> FEATURE:
<221> NAME/KEY: misc_feature
<222> LOCATION: ()..()
<223> OTHER INFORMATION: fusion protein

<400> SEQUENCE: 17

Ala Val Gln Pro Asp Gly Gly Gln Pro Ala Val Ser Tyr Ser Ile Thr
1               5                   10                  15

Thr Pro Ser Gln
            20

<210> SEQ ID NO 18
<211> LENGTH: 19
<212> TYPE: PRT
<213> ORGANISM: Artificial Sequence
<220> FEATURE:
<221> NAME/KEY: misc_feature
<222> LOCATION: ()..()
<223> OTHER INFORMATION: fusion protein

<400> SEQUENCE: 18

Val Gln Pro Asp Gly Gly Gln Pro Ala Val Ser Tyr Ser Ile Thr Thr
1               5                   10                  15

Pro Ser Gln

<210> SEQ ID NO 19
<211> LENGTH: 18
<212> TYPE: PRT
<213> ORGANISM: Artificial Sequence
<220> FEATURE:
<221> NAME/KEY: misc_feature
<222> LOCATION: ()..()
<223> OTHER INFORMATION: fusion protein

<400> SEQUENCE: 19

Gln Pro Asp Gly Gly Gln Pro Ala Val Ser Tyr Ser Ile Thr Thr Pro
1               5                   10                  15

Ser Gln

<210> SEQ ID NO 20
<211> LENGTH: 15
<212> TYPE: PRT
<213> ORGANISM: Artificial Sequence
<220> FEATURE:
<221> NAME/KEY: misc_feature
<222> LOCATION: ()..()
<223> OTHER INFORMATION: fusion protein

<400> SEQUENCE: 20

Gly Gly Gln Pro Ala Val Ser Tyr Ser Ile Thr Thr Pro Ser Gln
1               5                   10                  15

<210> SEQ ID NO 21
<211> LENGTH: 14
<212> TYPE: PRT
<213> ORGANISM: Artificial Sequence
<220> FEATURE:
<221> NAME/KEY: misc_feature
<222> LOCATION: ()..()
<223> OTHER INFORMATION: fusion protein

<400> SEQUENCE: 21

Gly Gln Pro Ala Val Ser Tyr Ser Ile Thr Thr Pro Ser Gln
1               5                   10
```

```
<210> SEQ ID NO 22
<211> LENGTH: 24
<212> TYPE: PRT
<213> ORGANISM: Artificial Sequence
<220> FEATURE:
<221> NAME/KEY: misc_feature
<222> LOCATION: ()..()
<223> OTHER INFORMATION: fusion protein

<400> SEQUENCE: 22

Gly Gln Pro Asp Gly Gly Gln Pro Ala Val Arg Asn Glu Arg Ala Thr
1               5                   10                  15

Tyr Ser Ile Thr Thr Pro Ser Gln
            20

<210> SEQ ID NO 23
<211> LENGTH: 13
<212> TYPE: PRT
<213> ORGANISM: Artificial Sequence
<220> FEATURE:
<221> NAME/KEY: misc_feature
<222> LOCATION: ()..()
<223> OTHER INFORMATION: fusion protein

<400> SEQUENCE: 23

Asn Glu Arg Ala Thr Tyr Ser Ile Thr Thr Pro Ser Gln
1               5                   10
```

PRODUCTION OF A PARVOVIRUS VACCINE IN PLANTS AS VIRAL COAT PROTEIN FUSIONS

This application is a continuation of patent application Ser. No. 09/520,967 now U.S. Pat. No. 6,730,306, filed Mar. 8, 2000.

BACKGROUND OF THE INVENTION

1. Field of the Invention

The present invention relates to the field of genetically engineered peptide production in plants, more specifically, to the use of tobamovirus vectors to express fusion proteins, and more specifically, to a vaccine comprising an encapsidated virus having a modified coat protein which displays a parvovirus antigen.

2. Description of the Background Art

Peptides are a diverse class of molecules having a variety of important chemical and biological properties. Some examples include; hormones, cytokines, immunoregulators, enzyme inhibitors, vaccine antigens, adhesion molecules, receptor binding domains, and the like. The cost of chemical synthesis limits the potential applications of synthetic peptides for many uses such as therapeutic drugs or vaccines. There is a need for inexpensive and rapid synthesis of milligram and larger quantities of naturally occurring polypeptides. Towards this goal many animal and bacterial viruses have been used successfully as peptide carriers.

The safe and inexpensive culture of plants provides an advantageous alternative for cost-effective production of pharmaceutically useful peptides. During the last decade, considerable progress has been made in expressing foreign genes in plants. Foreign proteins are now routinely produced in many plant species either for modification of the plant or for protein extraction and production. Animal proteins have been effectively produced in plants (reviewed in Krebbers, E. et al., In: *Plant Protein Engineering* (P. R. Shewry et al., eds.), Cambridge University Press, Cambridge, 1992, pp. 316–324).

Figure 1:
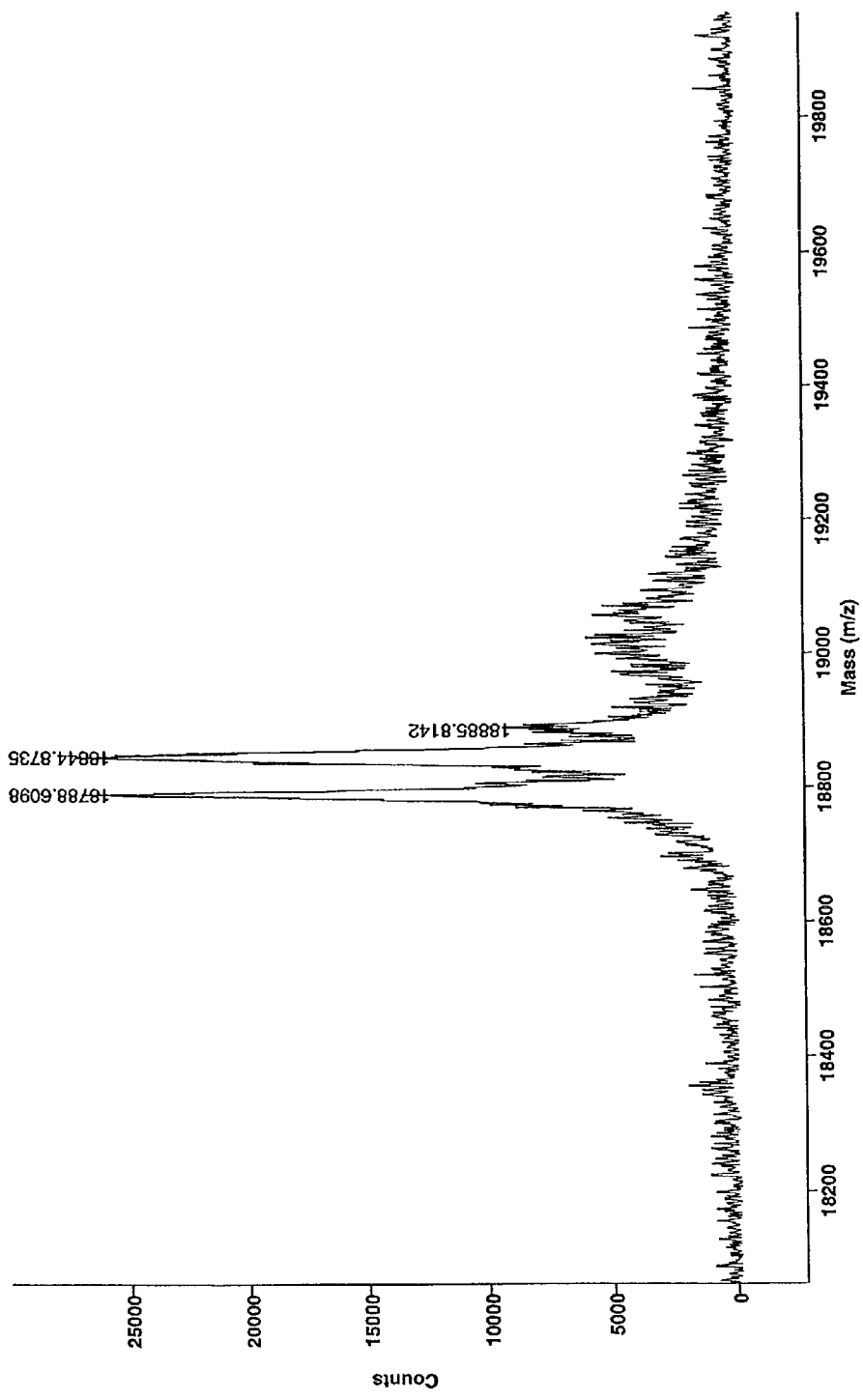

Vectors for the genetic manipulation of plants have been derived from several naturally occurring plant viruses, including tobacco mosaic virus (TMV). TMV is the type member of the tobamovirus group. TMV has straight tubular virions of approximately 300×18 nm with a 4 nm-diameter hollow canal, consisting of approximately 2000 units of a single capsid protein wound helically around a single RNA molecule. Virion particles are 95% protein and 5% RNA by weight. The genome of TMV is composed of a single-stranded RNA of 6395 nucleotides containing five large open reading frames (ORFs). Expression of each gene is regulated independently. The virion RNA serves as the messenger RNA (mRNA) for the 5' genes, encoding the 126 kDa replicase subunit and the overlapping 183 kDa replicase subunit that is produced by read-through of a UAG stop codon approximately 5% of the time. Expression of the internal genes is controlled by different promoters on the minus-sense RNA that direct synthesis of 3'-coterminal subgenomic mRNAs which are produced during replication (FIG. 1). A detailed description of tobamovirus gene expression and life cycle can be found, among other places, in Dawson and Lehto, *Adv. Vir. Res.* 38:307–342 (1991). It is of interest to provide new and improved vectors for the genetic manipulation of plants.

For production of specific proteins, transient expression of foreign genes in plants using virus-based vectors has several advantages. Products of plant viruses are among the highest produced proteins in plants. Often a viral gene product is the major protein produced in plant cells during virus replication. Many viruses are able to spread quickly from an initial infection site to almost all cells of the plant. For these reasons, plant viruses have been developed into efficient transient expression vectors for foreign genes in plants. Viruses of multi-cellular plants are relatively small, probably due to the size limitation in the pathways that allow viruses to move to adjacent cells in systemic infection of the entire plant. Most plant viruses have single-stranded RNA genomes of less than 10 kb. Genetically altered plant viruses provide one efficient means of transfecting plants with genes encoding peptide-carrier fusion proteins. A discussion of TMV coat protein fusions is provided in Turpen et al., U.S. Pat. No. 5,977,438 entitled "Production of Peptides in Plants as Viral Coat Protein Fusions." Nov. 2, 1999. See also: Yusibov V. et al., *Proc. Natl. Acad. Sci. USA* 94:5784–5788 (1997); Modelska, A et al., *Proc. Natl. Acad. Sci. USA* 95:2481–2485 (1998).

The pathogenesis of parvovirus infection has been most recently reviewed by Parish, C. R., *Baillieres Clin. Haematol.* 8:57–71, (1995.). Feline parvovirus (FPV) is closely related to canine parvovirus and the respective diseases are similar in pathogenesis. Parvovirus replicates first in the tonsils, and then spreads to its target cells: mitotically active intestinal crypt epithelial cells and bone marrow stem cells. Viremia lasts for less than 7 days before death or recovery. Clinical signs in cats include fever, vomiting, diarrhea, panleukopenia, acute shock and death. The disease outcome is proportional to the severity of the leukopenia; cats with severe panleukopenia will often die, while those with mild leukopenia will usually survive.

The VP2 (or E2) epitope of mink enteritis virus (MEV), which is closely related to FPV, has been previously expressed on the surface of cowpea mosaic virus, which was propagated on the leaves of the black-eyed bean (Dalsgaard, K et al., *Nature Biotechnol.* 15:248–252 (1997)). One mg of the cow pea mosaic virus material that expressed this epitope was used to immunize minks against virulent MEV. The minks were protected against clinical disease, and shed very little virus. The authors suggested that this epitope, expressed in this manner, could also be used to protect cats and dogs against their respective parvovirus infections.

The coding sequence for VP2 (E2) and the rabies spike glycoprotein have also been engineered into raccoon poxvirus to make a five recombinant vaccine against rabies and feline panleukopenia (Hu, L. et al., 1996. *Virology* 218: 248–252., Hu, L. et al., 1997, *Vaccine* 15:1466–1472.). Cats vaccinated with this construct showed excellent protection against virulent parvovirus challenge.

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

SUMMARY OF THE INVENTION

The present invention provides recombinant plant viruses that express fusion proteins that are formed by fusion between a plant viral coat protein (VCP) and a peptpide or polypeptide of interest, primarily a peptide that bears an epitope of FLV. By infecting plant cells with the recombinant plant viruses of the invention, relatively large quantities of the peptide, in the form of a fusion protein, is produced. The fusion protein encoded by the recombinant plant virus may be engineered to have a variety of structures. The peptide may be fused to the amino terminus (N-terminus) or to the carboxy-terminus (C-terminus) of the VCP. Alternatively, the peptide may be fused internally into a coat protein (so that it is flanked on either side by coat protein sequences). The VCP fusion protein should have one or more properties of the fused peptide/polypeptide. The recombinant coat fusion protein may be used as an immunogen or antigen to induce an antibody response and protective immunity, or as reagent for developing and conducting immunoassays.

This invention also provides a polynucleotide that includes the genome of a recombinant plant virus. In another aspect, the invention provides the coat fusion protein that is encoded by the recombinant plant virus. Yet another embodiment is a plant cell or a whole plant that has been infected with this recombinant plant virus.

In particular, the invention provides a polynucleotide encoding a fuision protein capable of being expressed in a plant or a plant cell, wherein the fusion protein comprises (a) a plant VCP from a single-stranded plus-sense RNA virus fused to a peptide of interest, preferably comprising the amino acid sequence MGSDGAVQPDGGQPAV [SEQ ID NO:1] or comprising the amino acid sequence MGQPDGGQPAVRNERAT [SEQ ID NO:2], and (b) a promoter functional in plants that is situated 5' to the fusion protein coding region.

The present invention is an important step forward in the art as it provides:

1. Stable, soluble, extractable TMV N-terminal coat protein fusion products useful as immunogens and vaccines.
2. The first description of a polyethyleneimine based virus extraction method.
3. High yields and stabilities of protein product based upon the plant hosts that express, and extraction methods that are used to purify, the product. The interplay of the particular production host and extraction methods that maximize the amount of undegraded product contribute to the high yields.
4. Specific and safe immunologically active epitopes decorating virus particles.

The novel aspects of this invention are not limited in application to the disclosed parvovirus vaccines, but rather are applicable to the highly efficient and inexpensive production of any relevant biologically active protein product for commercial use. The present inventors have shown that TMV-based vectors can express small antigenic peptides on the virion surface, that these virions can be easily and highly purified from infected leafs, and that an exemplary peptide (FPV-E2) provides the basis for a safe and efficacious vaccine requiring no further adjuvant over and above the immunogen itself. The interstitial fluid of tobacco plants infected with particular TMV vectors containing the appropriate gene is safe, without requiring further purification, for pharmaceutical use, for example for injection into cats as a parvovirus vaccine.

BRIEF DESCRIPTION OF THE DRAWINGS

FIG. 1 shows the mass spectrometric data for construct 149 grown in *Nicotiana benthamiana* and purified by pH and heat treatment.

FIG. 2 shows the mass spectrometric data for construct 149 grown in *Nicotiana tabacum* and purified by pH and heat treatment.

FIG. 3 shows the mass spectrometric data for construct 150 grown in *Nicotiana benthamiana* and purified by PEI treatment method.

FIG. 4 shows the mass spectrometric data for construct 150 grown in *Nicotiana benthamiana* and purified by pH and heat treatment.

FIG. 5 shows the mass spectrometric data for construct 149 grown in *Nicotiana tabacum* and purified by pH and heat treatment.

FIG. 6 shows the mass spectrometric data for construct 150 grown in *Nicotiana tabacum* and purified by pH and heat treatment.

DESCRIPTION OF THE PREFERRED EMBODIMENTS

The subject invention provides novel recombinant plant viruses include in their genetic material nucleotide sequences that encode fusion proteins that consist of a plant viral coat protein (VCP) and an additional peptide/polypeptide of interest. The peptides of particular interest are the feline parvovirus peptide designated E1, which has the amino acid sequence MGSDGAVQPDGGQPAV [SEQ ID NO:1], and E2 which has the amino acid sequence MGQPDGGQPAVRNERAT [SEQ ID NO:2] as well as similar polypeptides that provide protective immunity against parvovirus when produced as part of a VCP fusion.

The recombinant plant viruses of the invention permit systemic expression of the fusion protein in an infected plant. Thus by employing these recombinant plant viruses, large quantities of a peptide of interest (as fusion protein) may be produced.

The fusion proteins of the invention comprise: (i) a plant VCP and (ii) a peptide or polypeptide of interest. The plant VCP portion may be derived from the same virus from which the genome of the expression vector is primarily derived. That is, the coat protein is native with respect to the recombinant viral genome. Alternatively, the coat protein fusion partner may be heterologous, that is, non-native, in that it is derived from a virus different that that which contributes the recombinant viral genome. In a preferred embodiment, the 17.5 kDa coat protein of TMV is used in conjunction with a TMV-derived vector.

The peptide/polypeptide of interest in the protein may consist of a peptide of virtually any amino acid sequence, provided that the peptide does not significantly interfere with (1) the ability of the fusion protein to bind to a receptor molecule, including to antibodies and T cell receptors; (2) the ability to bind to the active site of an enzyme (3) the ability to induce an immune response, (4) or any of the biological activity which may be required of the fusion protein, including hormonal activity, immunoregulatory activity or metal chelating activity, just to name a few. The peptide of interest may also possess additional chemical or biological properties that have not been enumerated. The peptide for fusing may may be obtained by employing all or part of the amino acid residues of a protein known to have the desired properties. For example, an amino acid sequence of hepatitis B surface antigen may be used as the peptide of interest herein, yielding a fusion protein that shares antigenic properties with hepatitis B surface antigen. Detailed structural and functional information about many proteins are well known; this information may be used by the person of ordinary skill in the art in selecting a peptide or polypeptide for the present fusion proteins that will have desired properties.

The peptide/polypeptide of interest may vary in size and is defined herein as having as few as one amino acid residue to over several hundred amino acid residues. Preferably, the peptide in the subject fusion protein is less than 100 amino acid residues in size, more preferably, less than 50 residues. It will be appreciated by those of ordinary skill in the art that in some embodiments of this invention, the peptide of interest portion may need to exceed 100 residues in order to maintain the desired structure and properties. Preferably, the size of the peptide of interest in the fusion protein is minimized when possible provided of course that it retains the desired biological/chemical properties.

While this peptide may be derived from any of the variety of proteins, a preferred protein is one against which an immune response is desired, so that tht peptide serves as an antigen, preferably in immunogenic form. For example, the fusion protein, or a fragment thereof, may be injected into a mammal, along with a suitable adjuvant, to induce an immune response directed against the peptide of interest. The immune response against this peptide domain of the fusion protein has numerous advantages, such as protection against infection and the generation of antibodies useful in immunoassays.

The location (or locations) in the VCP where the peptide of interest is joined (fused) to the VCP is referred to herein as the "fusion joint." A given fusion protein may have one or two fusion joints. The fusion joint may be located at the C-terminus of the VCP where it is fused to the N-terminus of the peptide of interest. The fusion joint may be located at the N-terminus of the VCP where it is fused to the C-terminus of the peptide of interest. In other embodiments of the invention, the peptide of interest is located internally within the VCP; in this case, the fusion protein will have two fusion joints. This is termed an internal fusion protein. Internal fusion proteins may comprise an entire plant VCP or a fragment thereof that is "interrupted" by the peptide of interest. The fusion joints may be located at a variety of sites within a coat protein. The entire peptide may lie in the N-terminal portion or the C-terminal portion of the VCP. Suitable sites for the fusion joints may be determined either through routine systematic variation, testing the resultant internal fusion protein for the desired properties. Suitable sites for the fusion joints may also be determined by inspection of the three dimensional structure of the coat protein to determine sites for "insertion" of the peptide that will not significantly interfere with the structural and biological functions of the VCP portion of the fusion protein. Detailed three dimensional structures of plant VCPs and their orientation in the virus have been determined and are publicly available to a person of ordinary skill in the art. For example, a resolution model of the coat protein of Cucumber Green Mottle Mosaic Virus (a coat protein bearing strong structural similarities to other tobamovirus coat proteins) and the virus can be found in Wang and Stubbs, *J. Mol. Biol.* 239:371–384 (1994). Detailed structural information of TMV can be found, among other places, in Namba et al., *J. Mol. Biol.* 208:307–325 (1989) and Pattanayok and Stubbs, *J. Mol. Biol.* 228:516–528 (1998).

Knowledge of the three dimensional structure of a plant virus particle and the assembly process of the virus particle permits the person of ordinary skill in the art to design various VCP fusions of the invention, including insertions, and partial substitutions. For example, if the peptide of interest is hydrophilic, it may be appropriate to fuse the peptide to the TMV coat protein (TMVCP) region known to be oriented as a surface loop region. Likewise, α helical segments that maintain subunit contacts might be substituted for appropriate regions of the TMVCP helices or nucleic acid binding domains expressed in the region of the TMVCP oriented towards the genome.

Polynucleotide sequences encoding the subject fusion proteins may comprise a "leaky" stop codon at a fusion joint. The stop codon may be present as the codon immediately adjacent to the fusion joint, or may be located close (e.g., within 9 bases) of the codons encoding the fusion joint. The purpose for such a leaky stop codon is to maintain a desired ratio of fuision protein to wild type coat protein. A "leaky" stop codon does not always result in translational termination and is periodically translated. The frequency of initiation or termination at a given start/stop codon is context dependent. The ribosome scans from the 5'-end of a mRNA for the first ATG codon. If it is in a non-optimal sequence context, the ribosome will pass, at a certain frequency, to the next available start codon and initiate translation downstream of the first. Similarly, the first termination codon encountered during translation will not always function if it is in a particular sequence context. Consequently, many naturally occurring proteins exist as a population having heterogeneous N and/or C terminal extensions. By including a leaky stop codon at a fusion joint coding region in a recombinant viral vector encoding a VCP fusion protein, the vector may be used to produce both the longer fusion protein and a second shorter protein, e.g., the VCP itself. A leaky stop codon may be used at, or proximal to, the fusion joints of fusion proteins in which the peptide of interest portion is joined to the C-terminus of the coat protein region, whereby a single recombinant viral vector could produce both VCP fusion proteins and VCPs. Additionally, a leaky start codon may be used at or near the fusion joints to obtain a similar result. In the case of TMVCP, extensions at the N and C-terminus are localized to the surface of viral particles and can be expected to project away from the helical axis. An example of a leaky stop sequence occurs at the junction of the 126/183 kDa reading frames of TMV as was described years ago (Pelham, H. R. B., *Nature* 272:469–471 (1978). Skuzeski, J. M. et al., *J. Mol. Biol.* 20:365–373 (1991), defined necessary 3' context requirements of this region to confer leakiness of termination on a heterologous protein marker gene (β-glucuronidase) as CAR-YYA (R=purine; Y=pyrimidine).

In another embodiment of the invention, the fusion joints on the fusion proteins are designed to be cleavable by having an amino acid sequence that is a substrate for a protease. This permits separation and isolation of the peptide of interest by using a suitable proteolytic enzyme. The proteolytic enzyme may contact the fusion protein either in vitro or in vivo.

The expression of the fusion protein may be driven by any of a variety of promoters functional in the context of the recombinant plant viral vector and host plant. In a preferred embodiment plant viral subgenomic promoters are used (U.S. Pat. No. 5,316,931).

Recombinant DNA technologies have allowed the life cycle of numerous plant RNA viruses to be extended artificially through a DNA phase that facilitates manipulation of the viral genome. These techniques may be applied by the person of ordinary skill in the art in order make and use recombinant plant viruses of the invention. The entire cDNA of the TMV genome was cloned and functionally joined to a bacterial promoter in an *E. coli* plasmid (Dawson, W. O. et al., *Proc. Natl. Acad. Sci. USA* 83:1832–1836 (1986)). Infectious recombinant plant viral RNA transcripts may also be produced using other well known techniques, for example, commercially available RNA polymerases from T7, T3 or SP6. Precise replicas of the virion RNA can be produced in vitro with RNA polymerase and dinucleotide cap, m7GpppG. This not only allows manipulation of the viral genome for reverse genetics, but it also allows manipulation of the virus into a vector to express foreign genes. A method of producing plant RNA virus vectors based on manipulating RNA fragments with RNA ligase has proved to be impractical and is not widely used (Pelcher, L. E. et al., EP 67553A2 (1982). Detailed information on how to make and use recombinant RNA plant viruses can be found, among other places in U.S. Pat. No. 5,316,931 (Donson et al.), which is herein incorporated by reference. The invention provides nucleic acids that comprise a recombinant RNA plant vector for expression of the subject fusion proteins. The invention also provides for nucleic acids that comprise a portion or portions of the subject vectors. The vectors described in U.S. Pat. No. 5,316,931 are particularly preferred for expressing the fusion proteins of the invention.

This invention also provides virus particles that comprise the subject fusion proteins. The coat of the virus particles of the invention may consist entirely of VCP fusion protein. In another embodiment, the virus particle coat consists of a mixture of VCP fusion proteins and non-fused VCP, wherein the ratio of the two proteins may vary. As tobamovirus coat proteins may self-assemble into virus particles, the virus particles of the invention may be assembled either in vivo or in vitro. The virus particles may also be conveniently disassembled-using well known techniques so as to simplify the purification of the subject fusion proteins, or portions thereof.

The invention also provides recombinant plant cells comprising the subject fusion proteins and/or virus particles comprising the subject fusion proteins. These plant cells may be produced either by infecting plant cells (in culture or in whole plants) with the infectious recombinant virus particles of the invention or with polynucleotides comprising the genomes of the infectious virus particle of the invention. The recombinant plant cells of the invention have many uses, chief among which is serving as a source for the fusion coat proteins of the invention.

The peptide portion of the subject fusion proteins may comprise many different amino acid sequences, and accordingly may have different biological/chemical properties. In a preferred embodiment, the peptide portion of the fusion protein is a vaccine antigen. The surface of TMV particles and other tobamoviruses contain continuous epitopes of high antigenicity and segmental mobility thereby making TMV particles especially useful in inducing a desired immune response. These properties make the virus particles of the invention especially useful as carriers of foreign epitopes to mammalian immune systems.

While the recombinant RNA viruses of the invention may express numerous coat fusion proteins for use as vaccine antigens (or their precursors), an imporant embodiment is a vaccine composition against malaria. Human malaria is caused by the protozoan species *Plasmodium falciparum, P. vivax, P. ovale* and *P. malariae* and is transmitted in the sporozoite form by the Anopheles mosquito. Control of this disease will likely require safe and stable vaccines. Several peptide epitopes expressed during various stages of the parasite life cycle are thought to contribute to the induction of protective immunity in partially resistant individuals living in endemic areas and in individuals experimentally immunized with irradiated sporozoites.

When the fusion proteins of the invention, fragments thereof or viral particles expressing the proteins or fragments are to be administered in vivo, they are typically given as a pharmaceutical composition that includes a pharmaceutically acceptable carrier or excipient. Such as carrier can be any compatible, non-toxic substance suitable for delivery of the desired compounds to the body. Sterile water, alcohol, fats, waxes and inert solids may be included in the carrier. Pharmaceutically accepted buffering agents, dispersing agents, etc. may also be incorporated into the pharmaceutical composition. Additionally, when fusion proteins or fragments are used to induce immune responses (protective or otherwise), the formulation may comprise one or more immunological adjuvants in order to stimulate a more potent desired immune response.

Any of a number of routes of administration may be used when giving the compositions to an animal, including a human. The pharmaceutical compositions may be administered orally or parenterally, i.e., subcutaneously, intradermally, intramuscularly or intravenously. Compositions for parenteral administration comprise a solution of the fusion protein (or derivative) or a cocktail thereof dissolved in an acceptable carrier, preferably an aqueous carrier, e.g., water, buffered water, 0.4% saline, buffered saline, 0.3% glycerine and the like. These solutions are sterile and generally free of particulate matter. These compositions may be sterilized by conventional sterilization techniques. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, The concentration of fusion protein (or portion thereof) in these formulations can vary widely depending on the specific amino acid sequence and the desired biological activity, e.g., from less than about 0.5%, usually at least about 1% to as much as 15 or 20% by weight and will be selected primarily based on fluid volumes, viscosities, etc., in accordance with the particular mode of administration selected and the condition of the recipient.

Actual methods for preparing parenterally administrable compositions and adjustments necessary for administration to subjects are known or apparent to those skilled in the art and are described in more detail in, for example, Remington's Pharmaceutical Science, current edition, Mack Publishing Company, Easton, Pa., which is incorporated herein by reference.

Having now generally described the invention, the same will be more readily understood through reference to the following examples which are provided by way of illustration, and are not intended to be limiting of the present invention, unless specified.

EXAMPLES

The following present examples are based on a full length insert of wild type TMV (U1 strain) cloned in the vector pUC 18 with a T7 promoter sequence at the 5'-end and a KpnI site at the 3'-end (pSNC004, FIG. 2) or a similar plasmid pTMV304. Using the polymerase chain reaction (PCR) technique and primers WD29 (SEQ ID NO:3) and D1094 (SEQ ID NO:4), a 277 XmaI/HindIII amplification product was inserted with the 6140 bp XmaI/KpnI fragment from pTMV304 between the KpnI and HindIII sites of the common cloning vector pUC 18 to create pSNC004. The plasmid pTMV304 is available from the American Type Culture Collection, Rockville, Md. (ATCC Accession # 45138). The genome of the wild type TMV strain can be synthesized from pTMV304 using the SP6 polymerase, or from pSNC004 using the T7 polymerase. The wild type TMV strain can also be obtained from the American Type Culture Collection, Rockville, Md. (ATCC Accession No. PV135). The plasmid pBGC152, Kumagai, M., et al. (1993), is a derivative of pTMV304 and is used only as a cloning intermediate in the examples described below. The construction of each plasmid vector described in the examples below is diagrammed in FIG. 3.

Example 1

Construction of pJL 60.3

To facilitate cloning of TMV U1 CP fusions into an infectious TMV U1 cDNA backbone, the vector pJL 60.3 was constructed. The plasmid pJL 60.3 contains a full length infectious clone of TMV U1 with a small multiple cloning site polylinker:
taaatattcttaagccagtagtatgggatatccagtggtatgggatcctacagtatc [SEQ ID NO:5]containing two BstXI sites, CCAGTAGTATGG [SEQ ID NO:6] and CCAGTGGTATGG [SEQ ID NO:7], separated by a unique EcoRV site (GATATC), between the stop codon of the 30K protein gene and the start codon of the U1 CP.

To construct pJL 60.3, a 0.7 kb DNA fragment comprising the TMV U1 CP and 3' UTS was PCR amplified from pBTI 801 using the following primers:

kinased 5' primer JAL 72
tgggatatccagtggtatgggatcctacagtatacactactccatctcag [SEQ ID NO:8] and 3' primer JON 56
cgcgtacctgggcccctaccgggggtaacg [SEQ ID NO:9]pBTI 801 contains a full length infectious clone TMV U1, under the control of the T7 promoter sequence, in a pUC based plasmid. A KpnI restriction enzyme site lies at the 3' end of the viral cDNA, immediately followed by a self-processing ribozyme sequence from sattelite tobacco ringspot virus RNA. The presence of this self-processing ribozyme downstream of the TMV 3' end allows for the transcription of the TMV cDNA without prior linearization of the plasmid template DNA (with KpnI, for example)).

A 0.3 kb fragment of pBTI 801 was then PCR amplified using the following primers:

| 5' primer JON 52 (TMV U1 nts 5456–5482): ggcccatggaacttacagaagaagtcg | [SEQ ID NO:10] |
|---|---|
| kinased 3' primer JAL 73 ctggatatcccatactactggcttaagaatatttaaaacgaatccgattcggcgaca | [SEQ ID NO:11] |

The 0.7 kb PCR product, containing the EcoRV and BstXI site CCAGTGGTATGG [SEQ ID NO:7] upstream of the U1 CP ORF and 3' UTS, was then ligated to the 0.3 bp PCR products (which contained the 3' end of the TMV 30K protein gene and the BstXI site CCAGTAGTATGG [SEQ ID NO: 6] downstream of the 30K protein stop codon. The product of this ligation reaction was then used in a PCR with 5' primer JON 52 (shown above)
3' primer JON56 (shown above).
to generate a 1 kb PCR product. That product was digested with PacI and NcoI, and the digested DNA was electrophoresed on an agarose gel. The NcoI site is contained within the primer sequence of JON 52, and the PacI site is a unique restriction site in the TMV U1 CP gene sequence. The 0.4 kb PacI-NcoI fragment was then isolated from an agarose gel and ligated into a PacI-NcoI digested 8.8 kb fragment of pBTI 801 to generate pJL 60.3.

Again, the relevant feature of pJL 60.3 for the construction of pBTI 2149 and pBTI 2150 is the existence of the BstXI site CCAGTAGTATGG [SEQ ID NO:6] between the TMV 30K stop codon and the CP start codon.

Example 2

Construction of plasmid pBTI 2149

A 0.7 kb DNA fragment comprising the TMV U1 coat protein (CP) and 3' UTS was PCR amplified from p BTI 801 using the following primers:

| 5' primer JAL 149 cctggg<u>ccagtagtatggg</u>ttcagatggtgctgtacaaccagatggaggtcaaccag ctgtatcttacagtatcactactccatctcagtt | [SEQ ID NO:12] |
|---|---|

3' primer JON 56 (shown above)
JAL 149 contains the BstXI restriction enzyme site (underscored) for cloning purposes and the coding sequence for the parovirus epitope MGSDGAVQPDGGQPAV [SEQ ID NO:1] and TMV U1 nts 5715–5743). The amplified product comprising the parvovirus epitope fused to the U1 CP gene was digested with KpnI and BstXI and ligated into the 8.4 kb KpnI-BstXI fragment of pJL 60.3 to generate pBTI 2149.

Plasmid vectors pBTI 2149 encodes the recombinant virus having a fuision protein of MGSDGAVQPDGGQPAV [SEQ ID NO:1]fused to the N-terminus of the coat protein. Plasmid vectors pBTI 2149 was deposited at the ATCC on Feb. 17, 2000, under the Budapest Treaty. The deposit bears the ATCC accession #PTA-1403.

Example 3

Construction of plasmid pBTI 2150

A 0.7 kb DNA fragment comprising the TMV U1 coat protein (CP) and 3' UTS was PCR amplified from p801 (basically pTMV 204) using the following primers:

5' primer JAL 150
cctggg
<u>ccagtagtatggg</u>ttcagatggtgctgtacaaccagatggaggtcaaccag ctgtatcttacagtatcactactccatctcagtt [SEQ ID NO:13]
3' primer JON 56. (shown above)
(The "forward" primer JAL 150 contains a BstXI restriction enzyme site (underscored above) for cloning purposes, the coding sequence for the parovirus epitope MGQPDGGQPAVRNERAT [SEQ ID NO:2] and TMV U1 nts 5718–5743.) The amplified product comprising the parvovirus epitope fused to the U1 CP gene was digested with KpnI and BstXI and ligated into the 8.4 kb KpnI-BstXI fragment of pJL 60.3 to generate pBTI 2150.

Plasmid vectors pBTI 2150 encodes the recombinant virus having a fusion protein of MGQPDGGQPAVRNERAT [SEQ ID NO:2] fused to the N-terminus of the coat protein. Plasmid vectors pBTI 2150 was deposited at the ATCC on Feb. 17, 2000, under the Budapest Treaty. The deposit bears the ATCC accession # PTA-1404.

Example 4

Production of Virus TMV 149

The virus TMV 149 was produced by transcription of plasmid pBTI 2149. Infectious transcripts were synthesized from transcription reactions with T7 RNA polymerase in the presence of cap analog (7mGpppG) (New England Biolabs) according to the manufacturers instructions. Transcripts were used to inoculate *N. benthamiana* leaves which had been lightly dusted with carborundum (silicon carbide 400 mesh, Aldrich).

Example 5

Production of Virus TMV 150

The virus TMV 150 was produced by transcription of plasmid pBTI 2150. Infectious transcripts were synthesized from transcription reactions with T7 RNA polymerase in the presence of cap analog (8 mGpppG) (New England Biolabs) according to the manufacturers instructions. Transcripts were used to inoculate *N. benthamiana* leaves which had been lightly dusted with carborundum (silicon carbide 400 mesh, Aldrich).

Example 6

Extraction and Purification of TMV Coat Protein Fusion Virions

The two TMV coat fusion constructs were expressed in and extracted from *Nicotiana benthamiana* and/or *Nicotiana tabacum* using a pH-heat or PEI extraction method as described below, and in Table 1. Virus preparations were characterized using Matrix Assisted Laser Desorption Ionization—Time of Flight (MALDI-TOF) (Example 7; see also Table 2). Based upon the product masses determined by MALDI and polyacrylamide gel electrophoresis (PAGE) analysis, a proteolytic degradation profile was determined for each construct for any given host plant or extraction method used to produce the coat fusion product. (Sees Tables 2 and 3).

A. pH-Heat Extraction

*Nicotiana benthamiana* or *Nicotiana tabacum* cv MD609, produced in a growth rooms, were inoculated with TMV derivatives containing parvovirus epitopes fused to the Nterminus of the coat protein. Plants were harvested 2.5–5 weeks post inoculation after systemic spread of the virus. Leaf and stalk tissue (150 g) was macerated in a 1 L Waring blender for 2.0 minutes at the high setting with 300 ml of chilled, 0.04% $Na_2S_2O_5$. The macerated material was strained through four layers of cheesecloth to remove fibrous material. The resultant "green juice" was adjusted to a pH of 5.0 with $H_3PO_4$. The pH adjusted green juice was heated to 47° C. and held at this temperature for 5 minutes and then cooled to 15° C. The heat-treated green juice was centrifuged at 6,000×G for 3 minutes resulting in two fractions, supernatant 1 and pellet 1. The pellet 1 fraction was resuspended in distilled water using a volume of water equivalent to 1/z of the initial green juice volume. The resuspended pellet 1 was adjusted to a pH of 7.5 with NaOH and centrifuged at 6,000×G for 3 minutes resulting in two fractions, supernatant 2 and pellet 2. Virus was precipitated from both supernatant fractions 1 and 2 by the addition of polyethylene glycol (PEG) 6,000 and NaCl (4% by volume). After incubation at 4° C. (1 hour), precipitated virus was recovered by centrifugation at 10,000×G for 10 minutes. The virus pellet was resuspended in 10 mM $NaKPO_4$ buffer, pH 7.2 and clarified by centrifugation at 10,000×G for 3 minutes. The clarified virus preparation was precipitated a second time by the addition of polyethylene glycol (PEG) 6,000 and NaCl (4% by volume). Precipitated virus was recovered by centrifugation as described above. Virus yields are shown in Table 1.

B. Polyethyleneimine (PEI) Extraction

*Nicotiana benthamiana* or *Nicotiana tabacum* cv MD609, produced in a growth rooms, were inoculated with tobacco mosaic virus derivatives containing parvovirus epitopes fused to the Nterminus of the coat protein. Plants were harvested 2.5–5 weeks post inoculation after systemic spread of the virus. Leaf and stalk tissue (150 g) was macerated in a 1 L Waring blender for 2.0 minutes at the high setting with 300 ml of chilled, 50 mM Tris, pH 7.5, 2 mM EDTA and 0.1% β-mercaptoethanol. The macerated material was strained through four layers of cheesecloth to remove fibrous material. The resultant "green juice" was adjusted to 0.1% polyethylenimine, PEI (Sigma, St. Louis, Mo.) by the addition of a 10% PEI W/V stock solution. The PEI treated green juice was stirred for 30 minutes, (4° C.) and then centrifuged at 3,000×G for 5 minutes resulting in two fractions, supernatant 1 and pellet 1. The pellet 1 fraction was resuspended in distilled water using a volume of water equivalent to ½ of the initial green juice volume. The resuspended pellet 1 was adjusted to a pH of 7.5 with NaOH and centrifuiged at 6,000×G for 3 minutes resulting in two fractions, supernatant 2 and pellet 2. Virus was precipitated from both supernatant fractions 1 and 2 by the addition of polyethylene glycol (PEG) 6,000 and NaCl (4% by volume). After incubation at 4° C. (1 hour), precipitated virus was recovered by centrifugation at 10,000×G for 10 minutes. The virus pellet was resuspended in 10 mM $NaKPO_4$ buffer, pH 7.2 and clarified by centrifugation at 10,000×G for 3 minutes. The clarified virus preparation was precipitated a second time by the addition of polyethylene glycol (PEG) 6,000 and NaCl (4% by volume). Precipitated virus was recovered by centrifligation as described above. Virus yields are shown in Table 1.

TABLE 1

| | | Virus Yield | |
|---|---|---|---|
| Vector | Host Plant | Extraction Method | Virus Yield* |
| TMV149 | *N. benthamiana* | PH-Heat, Supernatant 1 | 0.3929 |
| TMV149 | *N. benthamiana* | PH-Heat, Supernatant 2 | 0.0396 |
| TMV149 | *N. benthamiana* | PEI, Supernatant 1 | 0.0005 |
| TMV149 | *N. benthamiana* | PEI, Supernatant 2 | — |
| TMV149 | *N. tabacum* | PH-Heat, Supernatant 1 | 0.0488 |
| TMV149 | *N. tabacum* | PH-Heat, Supernatant 2 | 0.0376 |
| TMV149 | *N. tabacum* | PEI, Supernatant 1 | — |
| TMV149 | *N. tabacum* | PEI, Supernatant 2 | — |
| TMV150 | *N. benthamiana* | PH-Heat, Supernatant 1 | 1.2274 |
| TMV150 | *N. benthamiana* | PEI, Supernatant 2 | 0.8860 |
| TMV150 | *N. benthamiana* | PEI, Supernatant 1 | 1.5369 |
| TMV150 | *N. tabacum* | PEI, Supernatant 2 | — |
| TMV150 | *N. tabacum* | PH-Heat, Supernatant 1 | 0.321 |
| TMV150 | *N. tabacum* | PEI, Supernatant 1 | 0.0368 |
| TMV150 | *N. tabacum* | PEI, Supernatant 2 | 0.0001 |

*virus yields are expressed as mg virus per g fresh weight, plant tissue extracted and were determined spectrophotometrically (absorbance at a260). all values were derived from the initial peg precipitates.

The yield of epitope specific virus particles is dependent upon the species of plant used as the virus host and method of extraction. TMV149 yielded the highest quantity of virus when produced in *N. benthamiana* and extracted using the pH-heat method. In addition, the TMV149 particles partitioned primarily into supernatantl. Negligible yields of TMV149 were observed when the PEI method was employed. TMV150 yielded the highest quantity of virus when produced in *N. benthamiana* and extracted using the PEI method. TMV150 partitioned into both supernatant 1 and 2 (60% and 40%, respectively) when extracted by the pH-heat method.

Example 7

Analysis of Coat Protein Fusions by MALDI

PEG precipitated, resuspended virus preparations were diluted in 50% acetonitrile and further diluted 1:1 with sinapinic acid (Aldrich, Milwaukee, Wis.). The sinapinic acid was prepared at a concentration of 10 mg/ml in 0.1% aqueous triflouroacetic acid/acetonitrile (70/30 by volume). The sinapinic acid treated sample (1.0 μl) was applied to a stainless steel MALDI plate surface and allowed to air dry at room temperature. MALDI-TOF mass spectra were obtained with a PerSeptive Biosystems DE-PRO (Houston, Tex.) operated in the linear mode. A pulsed laser operating at 337 rim was used in the delayed extraction mode for ionization. An acceleration voltage of 25 kV with a 90% grid voltage and a 0.1% guide wire voltage was used. Approximately 100 scans were acquired and averaged over the mass range 2,000–156,000 Da with a low mass gate of 2,000. Ion source and mirror pressures were approximately $1.2 \times 10^{-7}$ and $1.6 \times 10^{-7}$ Torr, respectively. All spectra were mass calibrated with a single-point fit using horse apomyoglobin (16,952 Da).

TABLE 3

Proteolytic Degradation Profiles

| | MW (daltons) | |
|---|---|---|
| TMV149 | | |
| GSDGAVQPDGGQPAVSYSITTPSQ | 18,816.5 | SEQ ID NO:14 |
| SDGAVQPDGGQPAVSYSITTPSQ | 18,759.5 | SEQ ID NO:15 |
| GAVQPDGGQPAVSYSITTPSQ | 18,557.4 | SEQ ID NO:16 |
| AVQPDGGQPAVSYSITTPSQ | 18,500.4 | SEQ ID NO:17 |
| VQPDGGQPAVSYSITTPSQ | 18,429.4 | SEQ ID NO:18 |
| QPDGGQPAVSYSITTPSQ | 18,330.3 | SEQ ID NO:19 |
| GGQPAVSYSITTPSQ | 17,990.2 | SEQ ID NO:20 |
| GQPAVSYSITTPSQ | 17,933.1 | SEQ ID NO:21 |
| TMV150 | | |
| GQPDGGQPAVRNERATYSITTPSQ | 19,027.7 | SEQ ID NO:22 |
| NERATYSITTPSQ | 17,965.1 | SEQ ID NO:23 |

Amino acids designated in bold are the natural N-terminal residues resident on TMV coat proteins.

Amino acids designated in bold are the natural N-terminal residues resident on TMV coat protein.

The results presented in Tables 2 and 3 indicate effects of host species, extraction method and extraction timing on the proteolysis of N-terminal TMV coat protein fusions. In all cases, the terminal Met residue is removed from all fusions, as is the case with native coat protein. The N-terminal glycine residue is removed from 40–60% of the TMV149 fusions. Extractions (pH-heat) performed on TMV149 and 150 produced in 17 day post inoculated *N. tabacum*, resulted in the most complex and greatest degree of proteolytic activity. The differences in proteolytic degradation may reflect both qualitative and quantitative differences in proteases present in different plant species or at different plant development periods. The PEI extraction of TMV 150 proved to be protective, resulting in negligible degradation relative to the pH-heat extraction (*N. tabacum* host).

TABLE 2

Product Mass Characterization

Figure 2:
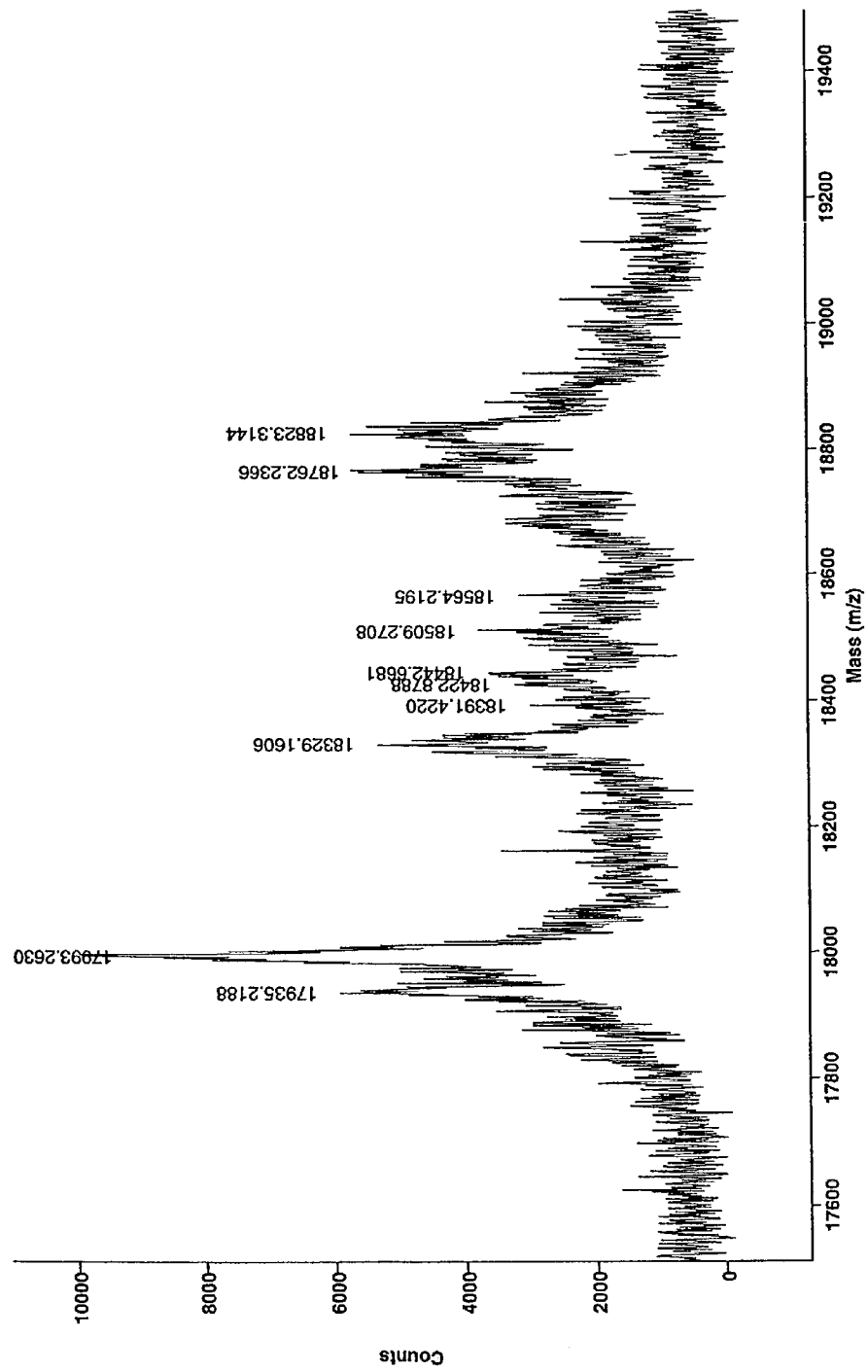
Figure 3:
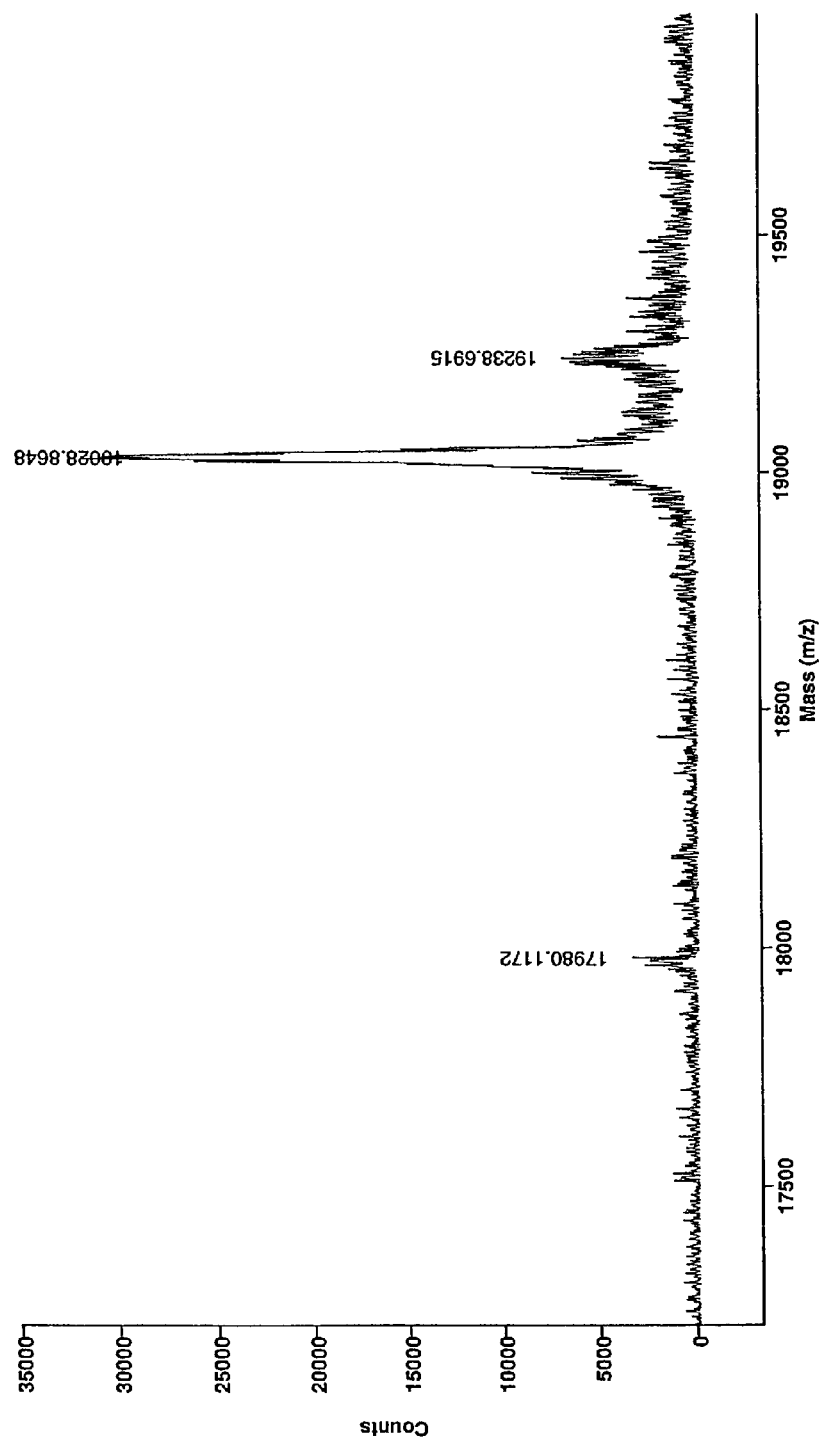
Figure 4:
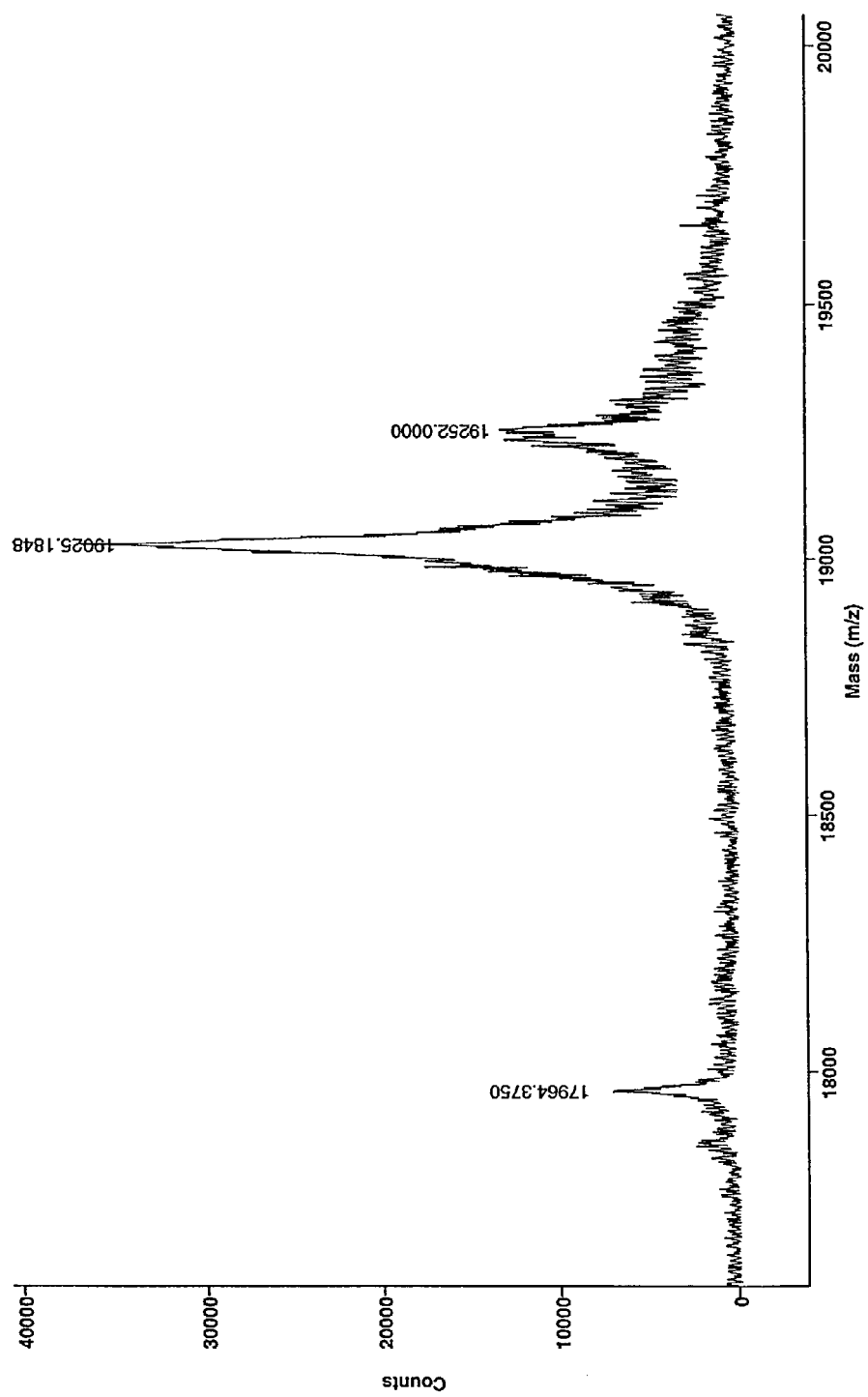
Figure 5:
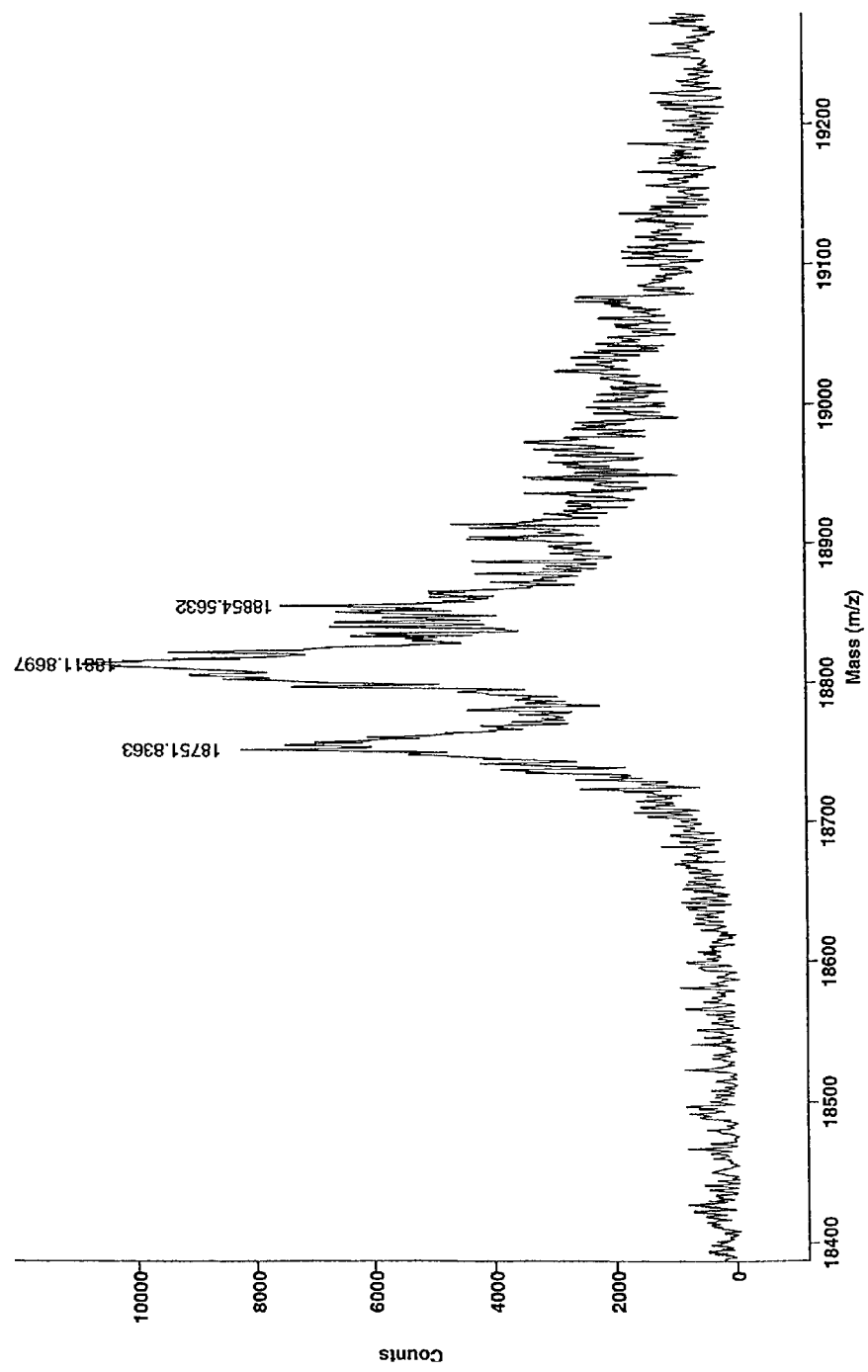

| Plant Host/Vector | Days Post Inoculation | Extraction Method and Fraction | Product Mass (MALDI) Daltons*,** |
|---|---|---|---|
| *N. benthamiana*/ TMV149 | 17 | PH-Heat Supernatant 1 | 18,822 (50%); 18,766 (50%)** FIG. 1 |
| *N. tabacum*/ TMV149 | 17 | PH-Heat Supernatant 1 | 18,823 (40%); 18,762 (40%) 18,564 (<2%); 18,509 (<2%); 18,442 (2%); 18,329 (<2%); 17,993 (10%); 17,935 (2%) FIG. 2 |
| *N. tabacum*/ TMV149 | 35 | PH-Heat, supernatant 1 | 18,812 (60%); 18,752 (40%) FIG. 5 |
| *N. benthamiana*/ TMV150 | 17 | PH-Heat, supernatant 1 | 19,025 (>95%); 17,964 (<5%) FIG. 4 |
| *N. benthamiana*/ TMV150 | 17 | PEI, Supernatant 1 | 19,029 (>95%); 17,980 (<5%) FIG. 3 |
| *N. tabacum*/ TMV150 | 17 | pH-Heat, Supernatant 1 | 19,020 (60%); 17,956 (40%)** FIG. 6 |
| *N. tabacum*/ TMV150 | 35 | pH-Heat, Supernatant 1 | 19,020 (80%); 17,956 (20%) |
| *N. tabacum*/ TMV150 | 17 | PEI, Supernatant 1 | 19,021 (>95%); 17,957 (<5%) |

*The number in parentheses is the approximate percentage of coat fusion present at that particular mass (based upon the analysis of fusion proteins separated by PAGE and stained with coomassie blue).
**Mass is corrected for Sodium ions (23 Daltons).

Example 8

Virion Purification and Formulation for Use in Animal Studies

PEG precipitated virion preparations (see Table 4) were resuspended in water for injection (WFI) at a concentration of 1.0 mg virus per 1.0 ml WFI. All laboratory ware used to process the virus preparations was baked at 225° C. for 18 hours. The resuspended virus preparation was solvent-extracted with chloroform and 1-butanol (8% by volume) by intermittent shaking for 1 hour at room temperature. Phases were separated by centrifugation at 10,000×G for 5 minutes. The aqueous phase was frozen in a dry ice/methanol bath and lyophilized overnight until dry. The lyophilized virus preparation was resuspended at a concentration of 5–10 mg virus per 1.0 ml WFI. The resuspended virus preparation was packaged in 10 ml serum vials that were sealed by crimping.

TABLE 4

TMV Fusions Preparations Processed for Animal Studies

| TMV Fusion | Host | Extraction Method |
|---|---|---|
| TMV149 | N. benthamiana | PH-Heat, Supernatant 1 |
| TMV150 | N. benthamiana | PEI, Supernatant 1 |

Samples selection for further processing was based on both yield and percentage of fusion that remained undegraded (based on MALDI analysis).

Example 9

Vaccine Testing

The parvovirus vaccine, utilizing tobacco plant expressed construct E1 and construct E2, was tested in young cats for safety and efficacy. E2 expressed on TMV particles proved to be safe and immunogenic by itself. E1 vaccine was somewhat less immunogenic. Cats vaccinated with E2, E1 or a mixture of E2 and E1 all showed significant protection against a 30% lethal dose of virulent FPV. No adjuvant was required other than what was provided by TMV proteins, some of which are known to act as superantigens (nonspecific immunostimulators). With the development and testing of this particular vaccine, the present inventors hve established the usefulness and advantages of the expression system for producing common feline vaccines.

The E1 and E2 epitopes are the two principal hemagglutinating and neutralizing antibody-inducing antigens on the surface of FPV. The sequences of the two epitopes overlap. Cats immunized with these epitopes will develop virus neutralizing antibodies and will be partially protected against challenge with virulent virus. Therefore, cats were immunized with either E1 or E2 peptides, or with both, and then monitored for the vaccine's safety, immunogenicity and efficacy.

Cats were immunized with 100–200 μg of each peptide, starting at 8–12 weeks of age, and with a second immunization 4 weeks later. They were then challenged orally with a large dose of virulent FPV. Both immunogens appeared completely safe, inducing no fever, depression or local reactions. Antibodies were measured using the enzyme-linked immunosorbent assay (ELISA). After the second immunization, significant titers of antibodies were detected in ELISA run against whole parvovirus. Cats receiving E1+E2 gave slightly higher responses than cats immunized with E1 or E2. After challenge, cats immunized with E2 (either alone or in combination with E1) appeared to be solidly protected, as evidenced by minimal signs of disease and no mortality, when compared to control cats immunized whit TMV alone (that did not express E2 or E1). It was concluded that the E2 peptide, when delivered on TMV particles was a safe and effective vaccine, and moreover, did not require additional adjuvants.

To summarize:
1. Cats immunized with E1-TMV or E2-TMV (100–200μg) made detectable antibody responses as measured by ELISA against whole feline panleukopenia virus (FPV).
2. The antibodyh response to 200 μg of E1-TMV or E2-TMV was greater than to 100 μg.
3. Cats immunized with a combination of E1-TMV and E2-TMV made better antibody responses than cats immunized with either protein alone.
4. Cats vaccinated with E2-TMV or E1-TMV+E2-TMV showed better protection to virulent parvovirus challenge than control cats that were unimmunized or immunized with TMV. E2-TMV was more protective than E1-TMV
5. Both E1-TMV and E2-TMV prevented mortality; E2-TMV was more effective at reducing morbidity. E2-TMV-immunized cats were significantly less febrile, showed few clinical signs of illness and were markely less leukopenic than unimmunized cats or or cats immunized with control TMV.
6. Immunity conferred by E2-TMV was not sterilizing, which is typical of killed parvovirus vaccines. Immunized cats showed mild signs of disease but had pronounced immunological memory.

---

What is claimed is:

1. A pharmaceutical composition comprising:
   (a) an immunochemical reagent comprising a fusion protein produced in a plant or a plant cell, wherein the fusion protein comprises:
      (i) a plant viral coat protein from a plant virus; and
      (ii) a peptide comprising amino acids MGQPDGGQ-PAVRNERAT (SEQ ID NO:2) or MGSDGAVQP-DGGQPAV (SEQ ID NO:1), fused to the coat protein;
   wherein said fusion protein elicits an immune response without an adjuvant; and
   (b) a pharmaceutically or veterinarially acceptable carrier or excipient.

2. A pharmaceutical composition comprising:
   (a) an immunochemical reagent comprising a recombinant plant virus, wherein at least one capsid of the coat protein is a fusion protein produced in a plant or a plant cell, wherein the fusion protein comprises;
      (i) a plant viral coat protein from a plant virus; and
      (ii) a peptide comprising amino acids MGQPDGGQ-PAVRNERAT (SEQ ID NO:2) or MGSDGAVQP-DGGQPAV (SEQ ID NO:1), fused to the coat protein;
   wherein said fusion protein elicits an immune response without an adjuvant; and
   (b) a pharmaceutically or veterinarially acceptable carrier or excipient.

3. The pharmaceutical composition of claim 1, wherein the fusion protein is in a recombinant plant virus.

4. The pharmaceutical composition of claim 1 or 2 wherein said peptide is fused to the N-terminus of the coat protein.

5. The pharmaceutical composition of claim 2, wherein the recombinant plant virus is a live virus.

6. A virus particle comprising a fusion protein, wherein the fusion protein comprises:
   (i) a plant viral coat protein from a plant virus; and
   (ii) a peptide comprising amino acids MGQPDGGQ-PAVRNERAT (SEQ ID NO:2) or MGSDGAVQPDG-GQPAV (SEQ ID NO:1), fused to the coat protein:
   wherein said fusion protein elicits an immune response without an adjuvant.

7. The virus of claim 6, wherein said virus is a tobamovirus.

8. A pharmaceutical composition comprising:
   (a) an immunochemical reagent comprising a fusion protein produced in a plant or a plant cell, wherein the fusion protein comprises:
      (i) a plant viral coat protein from a plant virus; and
      (ii) a peptide comprising amino acids MGQPDGGQ-PAVRNERAT (SEQ ID NO:2) or MGSDGAVQP-DGGQPAV (SEQ ID NO:1), fused to the coat protein;
   wherein said fusion protein elicits protective immunity without an adjuvant; and
   a pharmaceutically or veterinarially acceptable carrier or excipient.

9. A pharmaceutical composition comprising:
   (a) an immunochemical reagent comprising a recombinant plant virus, wherein at least one capsid of the coat protein is a fusion protein produced in a plant or a plant cell, wherein the fusion protein comprises:
      (i) a plant viral coat protein from a plant virus; and
      (ii) a peptide comprising amino acids MGQPDGGQ-PAVRNERAT (SEQ ID NO:2) or MGSDGAVQP-DGGQPAV (SEQ ID N:1), or a fragment of either fused to the coat protein;
   wherein said fusion protein elicits protective immunity without an adjuvant; and (b) pharmaceutically or veterinarially acceptable carrier or excipient.

10. The pharmaceutical composition of claim 8, wherein the fusion protein is in a recombinant plant virus.

11. The pharmaceutical composition of claim 8 or 9 wherein said peptide is fused to the N-terminus of the coat protein.

12. The pharmaceutical composition of claim 9, wherein the recombinant plant virus is a live virus.

13. A virus particle comprising a fusion protein, wherein the fusion protein comprises:

(i) a plant viral coat protein from a plant virus; and (ii) a peptide comprising amino acids MGQPDGGQ-PAVRNERAT (SEQ ID N:2) or MGSDGAVQPDG-GQPAV (SEQ ID NO:1), fused to the coat protein;

wherein said fusion protein elicits protective immunity without an adjuvant.

14. The virus of claim 13, where said virus is a tobamovirus.

15. The virus particle of claim 6 or 13, wherein said peptide is fused to the N-terminus of the coat protein.

* * * * *